United States Patent [19]

Halasz

[11] 4,213,598
[45] Jul. 22, 1980

[54] COMPACT SANITARY KIT PACKAGE

[75] Inventor: Peter R. Halasz, Los Angeles, Calif.

[73] Assignee: Bergen-Brunswig Corporation, Los Angeles, Calif.

[21] Appl. No.: 968,748

[22] Filed: Dec. 13, 1978

[51] Int. Cl.² .......................... B65D 5/10; B65D 5/06
[52] U.S. Cl. .................. 206/45.14; 220/416; 229/40; 206/45.19; 206/634
[58] Field of Search ................ 206/45.14, 45.19, 168, 206/194, 432, 434, 634; 220/416; 229/40, 52 B

[56] References Cited
U.S. PATENT DOCUMENTS

| | | | |
|---|---|---|---|
| 2,274,253 | 2/1942 | Howell | 206/45.14 |
| 3,050,230 | 8/1962 | Cohane | 206/45.19 |
| 3,298,513 | 1/1967 | Krooss | 206/434 |
| 3,397,796 | 8/1968 | Watts | 206/45.14 |
| 3,438,482 | 4/1969 | Hamilton | 220/416 |
| 3,443,681 | 5/1969 | Wysocki | 206/45.14 |
| 3,627,115 | 12/1971 | Samalon | 206/45.14 |
| 3,765,529 | 10/1973 | Mueller | 206/45.14 |
| 3,847,276 | 11/1974 | Lehner | 206/45.14 |
| 4,130,202 | 12/1978 | Champlin | 229/40 |
| 4,131,198 | 12/1978 | Fischer | 206/45.19 |

Primary Examiner—Herbert F. Ross
Attorney, Agent, or Firm—G. Donald Weber, Jr.

[57] ABSTRACT

There is provided a unique tray or package for presenting a sanitary (asceptic) container. The package is arranged so that the container and associated parts of the kit are presented in a specific and sequential manner so that a prescribed utilization of the container and associated apparatus is achieved and an asceptic condition is maintained.

13 Claims, 3 Drawing Figures

COMPACT SANITARY KIT PACKAGE

BACKGROUND

1. Field of the Invention

This invention is directed to a packaging concept, in general, and a packaging concept which is directly related to an aseptic packaging arrangement, in particular.

2. Prior Art

In performing many medical analyses or diagnoses, it is necessary or desirable to have a urine specimen from the patient. There are several methods of obtaining urine specimens. One such method is through the use of the "mid-stream" collection procedure. In the midstream method of obtaining the specimen, the patient monitors and completes the specimen taking essentially unattended by a physician or other medical professional. However, if adequate care and control are not maintained, the specimen can become contaminated, usually through the carelessness, neglect or ignorance of the patient. That is, the patient will frequently handle the specimen container in a manner such as by contacting the specimen container with the patient's hands or the like which causes the container to be contaminated. Consequently, it is highly desirable to provide a kit or suitable arrangement for presenting the specimen container as well as utilization instructions in a sequential manner which is substantially controlled so that the patient cannot inadvertently handle the container. Therefore, by providing a package which controls the access to the various parts of the kit and the specimen container so that a sequential utilization is established, a more controlled method of obtaining an uncontaminated specimen is provided.

There are known in the art, several types of packages which are directly related to aseptic or sanitary packaging conditions. Some of these sanitary packaging arrangements are directed as mid-stream collection of urine wherein aseptic urine specimens are obtained. The known mid-stream collection devices or kits currently on the market comprise a container with either a funnel or a handle associated therewith. Of the known kits on the market, all incorporate one or more shortcomings or weaknesses. For example, in the known catch kits which use rigid funnels, the container is packaged in a closed, sealed box or carton which does not permit the patient or the medical professional to view the apparatus for preliminary instructions. In addition, the cap for ultimately closing the container (as well as the funnel) can be fairly easily contaminated by the patient.

Another kit in this general market also uses a package which is at least partially transparent. However, the package is frequently difficult to open which tends to cause the patient to contaminate the container. In addition, the package is arranged in such a manner that the aseptic lid is easily contaminated by the patient.

Cross reference is made to co-pending application, Ser. No. 938,832, Sanitary Kit Package, by P. R. Halasz, filed on Sept. 1, 1978 and assigned to the common assignee.

SUMMARY OF THE INVENTION

The invention relates to an organized mid-stream collection kit which is simple and effective for use by a patient to provide an aseptic specimen. The unique tray, which includes a tear strip for easy opening of the tray, folds out to readily present the specimen container.

The package comprises a plurality of panels which are interconnected to securely support and retain the specimen container and to present the container to a user is a specified manner. Also, the container lid is located beneath the container with the threaded portion protected. The panels of the tray interlock to all parts of the container kit in a predetermined relationship. The aseptic specimen container is presented in a controlled fashion wherein inadvertent contamination by the user is virtually impossible. The entire package is cased in polypropylene film to maintain the aseptic condition. In addition, the product of the package is stackable and shippable in standard commerce and storage areas.

DESCRIPTION OF A PREFERRED EMBODIMENT

Figure 1:
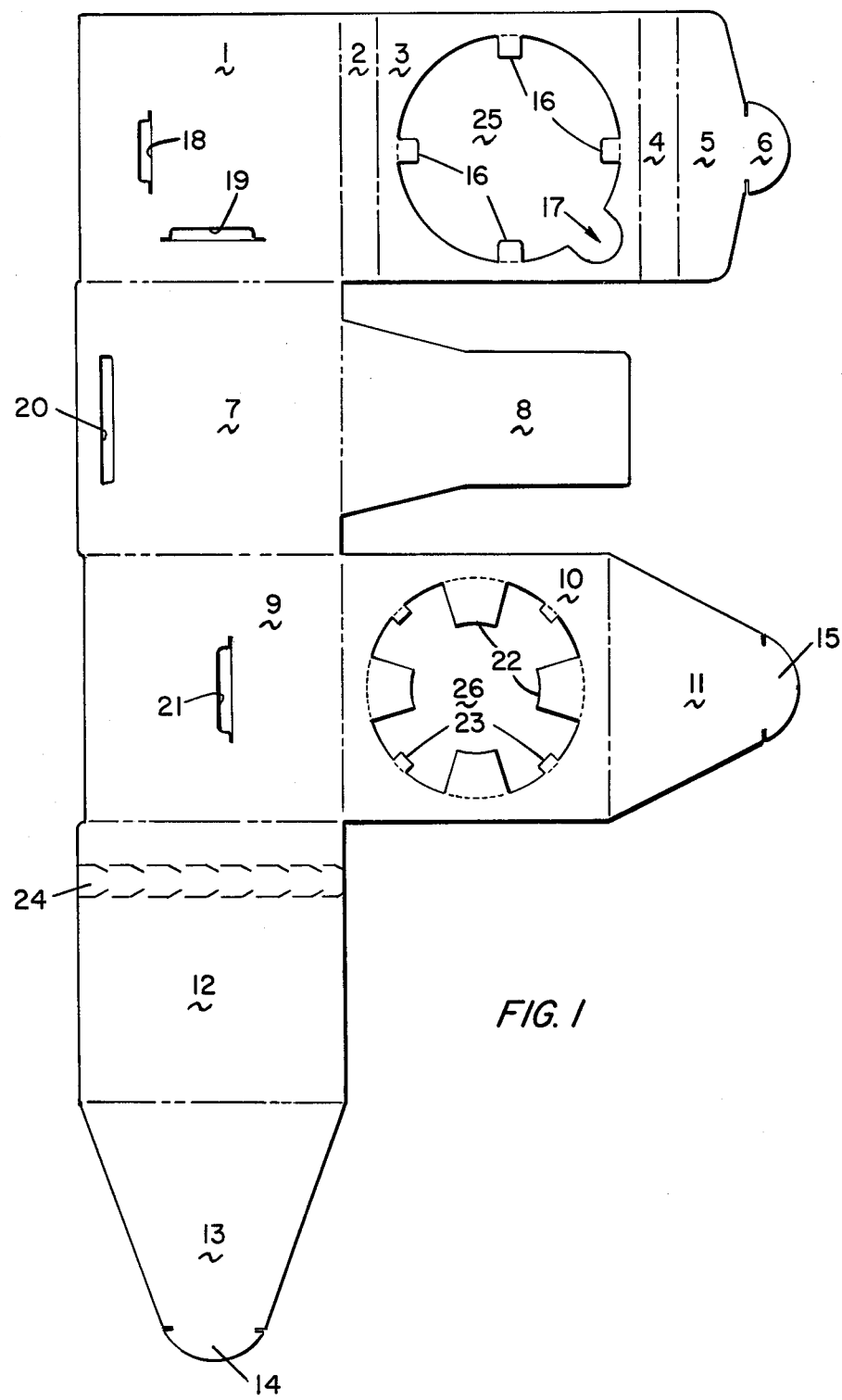
FIG. 1 is a plan view of the blank which is used to make the tray.

Referring now to FIG. 1, there is shown a plan view of the blank used to produce the tray of the instant invention. The tray comprises a plurality of panels which are connected together at prescored edges. Rectangular bottom panel 1 is substantially square in configuration and includes slots 18 and 19 therein. Shelf panel 3 is of substantially the same size and configuration as bottom panel 1. Shelf panel 3 includes a large opening 25 therein. Friction tabs 16 extend into opening 25 while an extended opening 17 protrudes from opening 25. Tabs 16 are prescored at the junction thereof with shelf panel 3 so that tabs 16 can be readily displaced as described hereinafter. Shelf side (spacer) panels 2 and 4 are joined to the edges of shelf panel 3. Panel 2 is also joined to bottom panel 1. Bottom closure panel 5 is joined to shelf side panel 4 and includes locking tab 6 which extends therefrom.

Side panel 7 is joined to one side of bottom panel 1 and includes slot 20 therein. Side panel 7 is also substantially square in configuration. Tongue panel 8 extends from one side of side panel 7 (essentially alongside of shelf panel 3 and the associated parts). Tongue or retainer panel 8, in a preferred embodiment, has a wider end connected to side panel 7 and a relatively narrower free end.

Connected to the other side of side panel 7 is top panel 9. Top panel 9 is of substantially the same size and shape as bottom panel 1. In addition, top panel 9 includes slot 21 therein. Flap panel 10 is joined to one edge of top panel 9 and extends in the same direction as panels 3 and 8. Flap panel 10 includes opening 26 therein. Tabs 22 and 23 extend into opening 26. Tabs 22 are prescored to permit them to bend readily. Tabs 23 provide a rigid gripping function. Closing top panel 11 extends from the opposite edge of panel 10 and includes locking tab 15.

The other side panel 12 extends from the opposite side of top panel 9. Side panel 12 is of substantially the same size and shape as side panel 7. Side panel 12 includes tear strip 24 therein. Bottom closure panel 13 and locking tab 14 extend from the edge of side panel 12.

Figure 2:
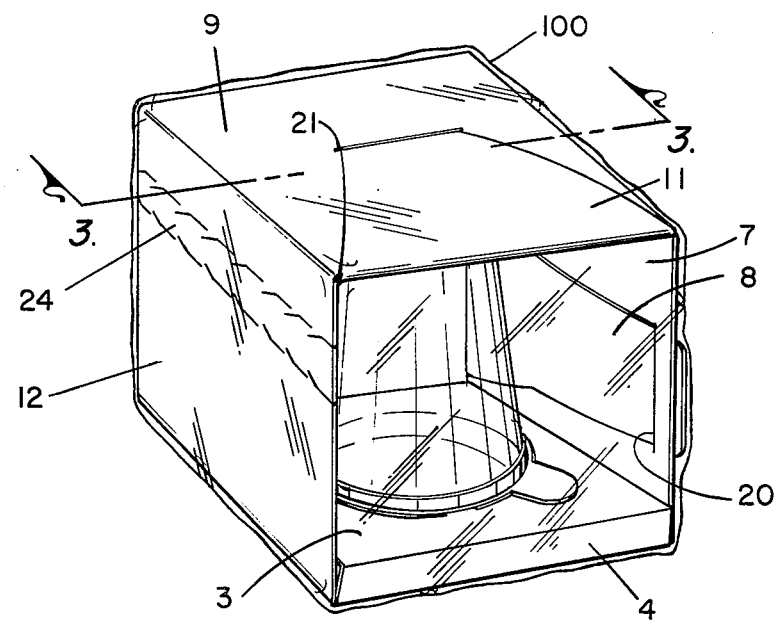
FIG. 2 is a perspective view of the fully assembled package including the protective film.
Figure 3:
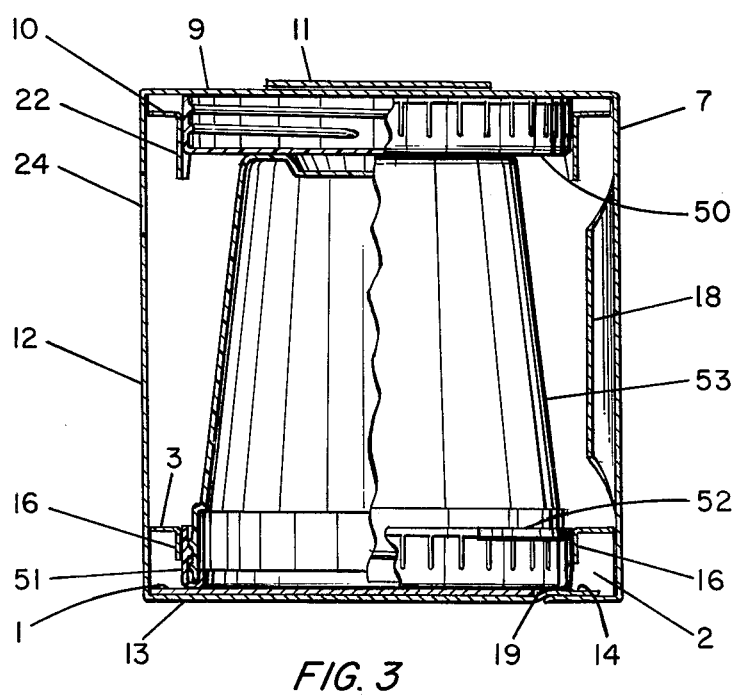
FIG. 3 is a cross-sectional view of the tray fully assembled and retaining a container.

Reference is concurrently made to FIGS. 1, 2 and 3 to describe the assembly of the package. Initially, it is assumed that all panels are joined at properly scored lines or edges. Typically, lid 50 is placed on panel 9 with the open, threaded side down. Flap panel 10 is then folded over panel 9 such that tabs 22 are bent upwardly by lid 50 and form a friction fit therewith. Similarly, tabs 23 also grip lid 50 firmly. Closure top panel 11 is folded around the edge of top panel 9. Locking tab 15 on panel 11 is inserted into slot 21 whereby panels 9 and 10 and 11 are substantially parallel to each other. In addition, lid 50 is retained between panels 9 and 10 with the threaded (interior) side thereof protected and maintained aseptic.

Also, panel 8 is folded over panel 7 and the smaller end of panel 8 is inserted into slot 20. Panel 8, thus, serves to retain any appropriate material such as towlette packs, I.D. material or the like.

Panel 2 is folded to be upright with respect to panel 1. Also, panel 3 is folded at a right angle to panel 2 and is, therefore, substantially parallel to panel 1. Panel 4 is folded at a right angle to panel 3 and, essentially, returns to panel 1. Panel 5 is then folded around the edge of panel 1 and tab 6 is inserted into slot 18. Thus, a shelf-like arrangement is formed with shelf panel 3 spaced from, and parallel to, panel 1.

Cup 53 with collar 51 threadedly engaged therewith is placed into opening 25 in shelf panel 3. Collar 51 engages tabs 16 which fold to the extent necessary. Tabs 16 thereby provide a force fit with collar 51. In addition tab 52 on collar 51 is inserted, through slot 17, under shelf panel 3. Thus, the combination of tab 17 (on collar 52) and tabs 16 (on shelf panel 3) maintain collar 52 and cup 53 firmly in place. Moreover, the open end of cup 53 is protected from contact by the user and remains sterile.

Now, panels 1, 7, 9, 12 and 13 are folded substantially normal to each other with panel 13 overlapping and outside of panel 1. Locking tab 14 is then inserted into slot 19 to close the package.

The package is now enveloped in a suitable outer film or layer 100. In a preferred embodiment, layer 100 is a film of polypropylene which is relatively tough and durable but is also transparent. The film is placed around the package and sealed by a suitable thermal sealing element wherein the package/kit is securely sealed but the inner parts are fully visible to the user. The entire apparatus is then placed in a suitable sterilization apparatus which is known in the art and which applies a relatively low temperature through the kit in an ethylene atmosphere which is a known sterilizing technique. Thus, the sealed package is sterilized.

When the package has been assembled as shown in FIG. 2, a totally sanitary unit is maintained and contained therein. For the patient to utilize the collection apparatus, the sterile package is opened by first removing the polypropylene film 100. The tear strip 24 is then removed by the patient, wherein the package is, effectively, severed and a three-panel unit produced. Basically, panel 1 remains flat with cup 53 extending upwardly therefrom. In addition, panels 7 and 9 tend to lie flat thereby giving access to the materials stored by panels 7 and 8 as well as to the outer surface of lid 50.

The patient, after performing the appropriate preliminary procedures, grasps cup 51 and removes same from shelf-panel 3, for example by aligning tab 52 with slot 17 and lifting. After the specimen has been collected, collar 51 is removed without touching the lip of cup 53 and discarded. Lid 50 is then grasped at its outer surface and, without contacting the inner, sterile surface, screwed onto cup 53. Thus, a specimen can be collected without contamination by the patient.

Thus, there is shown and described an organized tray (package) which requires that the user or patient follow instructions explicitly and, thereby, prevents contamination of the specimen container. In addition, the package protects and secures the components in such a manner that they will not fall apart and be inadvertently exposed to contamination when the patient takes them out of the package. Along the same lines, because of the package construction, only the outer surfaces of the container apparatus are readily available to the user, which again improves the contamination-avoidance aspect. The package provides transparent ends through which a patient can observe the apparatus and be preliminarily instructed by any professional personnel. Of course, while the invention has been described in terms of a urine specimen container, the package can be directed to other types of specimen containers if so desirable. Moreover, the package, when fully assembled is a relatively neat and geometrically regular package which readily lends itself to stackability, storage and transportation. While those skilled in the art may conceive modifications to the instant invention, any such modifications which fall within the purview of this description are intended to be included as well. The description is intended to be illustrative only and not limitative. The scope of the invention is limited only by the scope of the claims appended hereto.

Having thus described a preferred embodiment of the instant invention, what is claimed is:

1. A specimen container package comprising, top panel means, first component retaining panel means joined to one edge of said top panel means and including first locking means for locking said top panel means and said first component retaining panel means in parallel overlapping relationship, first and second side panel means joined to opposite edges of said top panel means to form sides of said package, one of said first and second panels having an aperture therein, bottom panel means joined to one of said first and second side panel means, first tab panel means connected to an edge of said one of said first and second side panel means for insertion into said aperture in said one side panel means, and second component retaining panel means joined to said bottom panel means and including second locking means for locking said bottom panel means and said second component retaining panel means together in parallel relationship.

2. The package recited in claim 1 including spacer panels connected to said second component retaining panel to maintain said second component retaining panel means and said bottom panel means in spaced apart, substantially parallel relationship.

3. The package recited in claim 1 wherein said first and second component retaining panel means include apertures therein for retaining said components.

4. The package recited in claim 1 wherein at least one of said first and second side panel means includes a tear-strip for opening said package.

5. The package recited in claim 1 including
lock tab means joined to one of said first and second side panel means for interlocking with said bottom panel means.

6. The package recited in claim 4 including
a plurality of tabs extending into the respective apertures in said first and second component retaining panel means.

7. The package recited in claim 1 including,
sealing means surrounding the assembled package to protect the inner portions thereof from inadvertent contamination.

8. The package recited in claim 6 wherein,
said bottom panel includes a pair of slots therein for engaging said lock tab means and said second locking means, respectively.

9. The package recited in claim 1 wherein,
said first tab panel means is wider at the end which is connected to said one side panel means than at the end which is inserted into the aperture in said one side panel means.

10. The package recited in claim 1 wherein,
said first locking means comprises a flap connected to said first component retaining panel means.

11. The package recited in claim 1 wherein,
said top panel means includes a slot therein for engaging said first locking means.

12. The package recited in claim 5 wherein,
said top panel means, said bottom panel means and the side panel means without said tear-strip tend to lie flat to expose the components retained by said first and second component retaining means when said tear-strip is removed.

13. The package recited in claim 1 wherein,
said first and said second component retaining panel means and said tab panel means are located on the same side of said package.

* * * * *